United States Patent
Lentz et al.

(10) Patent No.: US 10,159,822 B2
(45) Date of Patent: Dec. 25, 2018

(54) CATHETER AND TREATMENT METHODS FOR LOWER LEG ISCHEMIA

(71) Applicant: Cook Medical Technologies LLC, Bloomington, IN (US)

(72) Inventors: David Christian Lentz, Bloomington, IN (US); Christopher Michael Mobley, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 224 days.

(21) Appl. No.: 15/185,138

(22) Filed: Jun. 17, 2016

(65) Prior Publication Data
US 2016/0287845 A1    Oct. 6, 2016

Related U.S. Application Data

(62) Division of application No. 13/486,048, filed on Jun. 1, 2012, now abandoned.

(60) Provisional application No. 61/492,453, filed on Jun. 2, 2011.

(51) Int. Cl.
| A61M 25/10 | (2013.01) |
| A61M 5/14  | (2006.01) |
| A61M 25/00 | (2006.01) |
| A61M 25/01 | (2006.01) |
| A61M 25/09 | (2006.01) |
| A61M 29/02 | (2006.01) |

(52) U.S. Cl.
CPC ............ *A61M 25/104* (2013.01); *A61M 5/14* (2013.01); *A61M 25/002* (2013.01); *A61M 25/0102* (2013.01); *A61M 25/0108* (2013.01); *A61M 25/09* (2013.01); *A61M 29/02* (2013.01); *A61M 2025/0042* (2013.01); *A61M 2025/1061* (2013.01)

(58) Field of Classification Search
CPC ............ A61M 25/002; A61M 25/0102; A61M 25/0169; A61M 25/0172; A61M 25/10; A61M 25/104; A61M 2025/0042; A61M 2025/0183; A61M 2025/0681; A61M 2025/1052; A61M 2210/086
See application file for complete search history.

(56) References Cited

U.S. PATENT DOCUMENTS

| 4,029,104 A | 6/1977 | Kerber |
| 4,213,461 A | 7/1980 | Pevsner |
| 4,254,774 A | 3/1981 | Boretos |
| 4,327,734 A | 5/1982 | White, Jr. |

(Continued)

*Primary Examiner* — Kami A Bosworth
(74) *Attorney, Agent, or Firm* — Liell & McNeil

(57) ABSTRACT

A method of treating lower leg ischemia in a patient includes advancing a wire guide upstream through a vascular access sheath extending into an artery of the patient at a percutaneous entry point in the lower leg, and increasing a downstream flow of blood through the artery at least in part by dilating a constriction in the artery with a treatment mechanism guided into the constriction via the wire guide. A low profile balloon may be used as the treatment mechanism, and is advanced through the artery while the vascular access sheath protects the artery from irritation such that spasm of the artery is less likely to occur. Reduced risk of spasm advantageously enables retrograde access to chronic total occlusions such that multiple entry points into a patient's body are not necessary.

19 Claims, 6 Drawing Sheets

(56) References Cited

U.S. PATENT DOCUMENTS

| | | | |
|---|---|---|---|
| 4,896,669 A | 1/1990 | Bhate et al. | |
| 4,983,167 A | 1/1991 | Sahota | |
| 5,312,415 A | 5/1994 | Palermo | |
| 5,380,290 A * | 1/1995 | Makower | A61M 25/06 604/160 |
| 5,569,184 A | 10/1996 | Crocker et al. | |
| 5,752,934 A | 5/1998 | Campbell et al. | |
| 5,817,057 A | 10/1998 | Berenstein et al. | |
| 5,893,839 A * | 4/1999 | Johnson | A61M 37/00 424/424 |
| 6,379,319 B1 | 4/2002 | Garibotto et al. | |
| 6,709,444 B1 | 3/2004 | Makower | |
| 6,733,487 B2 | 5/2004 | Keith et al. | |
| 2002/0138129 A1 * | 9/2002 | Armstrong | A61F 2/07 623/1.11 |
| 2002/0173817 A1 | 11/2002 | Kletschka et al. | |
| 2003/0009190 A1 | 1/2003 | Kletschka et al. | |
| 2003/0208221 A1 | 11/2003 | El-Nounou | |
| 2004/0213770 A1 * | 10/2004 | Seward | A61K 35/28 424/93.71 |
| 2005/0171478 A1 | 8/2005 | Selmon et al. | |
| 2006/0015134 A1 | 1/2006 | Trinidad | |
| 2006/0184016 A1 * | 8/2006 | Glossop | A61B 1/2676 600/434 |
| 2007/0049867 A1 | 3/2007 | Shindelman | |
| 2007/0060863 A1 | 3/2007 | Goeken et al. | |
| 2007/0066975 A1 | 3/2007 | Wong et al. | |
| 2007/0208368 A1 | 9/2007 | Katoh et al. | |
| 2008/0154172 A1 | 6/2008 | Mauch | |
| 2009/0018566 A1 * | 1/2009 | Escudero | A61B 17/320758 606/159 |
| 2009/0234282 A1 | 9/2009 | McAndrew et al. | |
| 2009/0287166 A1 * | 11/2009 | Dang | A61M 25/00 604/265 |
| 2010/0125244 A1 * | 5/2010 | McAndrew | A61M 25/10 604/98.01 |
| 2010/0137899 A1 * | 6/2010 | Razack | A61M 29/02 606/200 |
| 2011/0022057 A1 * | 1/2011 | Eigler | A61B 17/3468 606/129 |
| 2011/0224606 A1 * | 9/2011 | Shome | A61M 25/104 604/96.01 |
| 2011/0319754 A1 * | 12/2011 | Solar | A61F 7/12 600/433 |
| 2012/0310209 A1 | 12/2012 | Lentz et al. | |

\* cited by examiner

CATHETER AND TREATMENT METHODS FOR LOWER LEG ISCHEMIA

TECHNICAL FIELD

The present disclosure relates generally to transluminal treatment of vascular constrictions, and relates more particularly to methodology and devices for treating lower leg ischemia from a percutaneous entry point in the lower leg.

BACKGROUND

Angioplasty utilizing catheters having inflatable balloons is a standard practice for treating obstructed vessels within the human anatomy. In a conventional approach, a catheter is advanced through an entry point in the patient's skin and slid over a wire guide to a desired location within the patient's vasculature. The balloon is thereby placed within an obstruction in the vessel, and then inflated to dilate the obstruction and increase or restore blood flow. Angioplasty has been used in various forms with great success for decades. As with other interventional techniques, clinicians continue to seek the capability to treat smaller vessels, and those located in more difficult to access places within the human body. Recent advancements have allowed angioplasty devices to traverse greater lengths within the body and reach constrictions within especially small vessels. Reaching a treatment location may be of little use, however, unless the associated wire guide over which the device travels is able to successfully cross a constriction to enable advancing the device into or past the same. Those skilled in the art will be familiar with the relative difficulty in certain instances of pushing a wire guide through material of a lesion blocking a vein or artery.

In the case of treating infrapopliteal arteries, for instance, matters may be further complicated by the location and nature of the disease. A significant challenge for a treating physician is the ability to cross obstructed areas in these vessels from a vascular access site that is relatively far away. In one conventional approach, an introducer sheath is inserted retrograde to blood flow in the femoral artery on the leg opposite the one to be treated. The introducer sheath and a wire guide are navigated together up through the iliac and then steered down into the opposite iliac artery. The sheath and wire are then typically further advanced as far as possible without being obstructed by the patient's anatomy or becoming too occlusive. From this point, the wire guide may be advanced by itself through the diseased vessel of interest, such as the popliteal artery, the anterior tibial, posterior tibial or peroneal artery.

Crossing lesions in the diseased vessel from such a distant access site can prove to be quite difficult. Each twist and turn through the torturous path navigated just to reach the diseased vessel can diminish the pushability of the wire. Each curve generates a certain amount of friction on the wire, and the cumulative effect of the friction from many turns can result in it being quite difficult to transmit force from where the wire is being pushed, outside the patient, to the distal tip attempting to push through the lesion. Should the diseased vessel have a chronic total occlusion (CTO), the wire guide may need to punch through a fibrous thrombus cap at the distal end of the lesion. These fibrous caps may be especially difficult to puncture given the conventional wire guide's atraumatic distal tip. The entry point of the cap is rarely in a fixed position, and the physician may not with any certainty be able to tell if she is pushing her way through the cap, going through the subintimal arterial layer, or perforating the vessel wall.

Alternative approaches access the vessel to be treated through the same leg femoral artery anterograde to blood flow. In certain instances, this strategy may be advantageous as there is a relatively straight approach and shorter distance to the lesion to be treated. Force may be more readily transmitted through the wire guide, and steering may be easier. The challenge of crossing a fibrous thrombus cap is not significantly diminished, however. Moreover, the external anatomy of the patient may not be conducive to this type of technique.

A relatively newer technique for crossing challenging lesions involves accessing the diseased infrapoplitieal artery from the calf or foot and traversing the lesion retrograde to blood flow. The wire can be advanced through the true lumen of the vessel and is more readily capable of puncturing the fibrous cap at the distal end of the lesion given the fairly short, straight approach and direct access to the fibrous cap. As an alternative to puncturing through the fibrous cap, the wire guide is sometimes taken subintimally and then re-enters the vessel on the other side. In either case, once the wire guide has successfully crossed, it can be captured with a snare and sheath placed above the lesion, i.e. upstream, and introduced into the patient's body via the same-leg or contralateral leg approaches discussed above. Once captured, the wire is pulled out of the anterograde sheath and then is utilized for primary treatment such as anterograde guiding of an angioplasty catheter.

Conventional strategies for accessing a diseased artery from the calf or foot and traversing the lesion in an upstream direction are not without risk or complications. Grasping the wire from upstream the lesion is by no means certain, and in any event typically requires a high degree of interventional skill. Should the wire guide cross the lesion subintimally, it must still be navigated back into the true lumen upstream of the lesion. This may be especially problematic where the lesion resides near one of the main tibial bifurcations. Further still, spasming of the vessel at or near the access point may result from the rubbing and friction of the wire, resulting in a compromised procedure and the potential loss of a good conduit should a vascular bypass graft later be desired. Certain attempts have also been made to advance a treatment mechanism such as a balloon catheter retrograde to blood flow through the arteries in the lower leg. These techniques too have shortcomings, particularly in relation to irritating the vessel with the catheter and/or wire guide and inducing spasm.

SUMMARY OF THE DISCLOSURE

In one aspect, a method of treating lower leg ischemia in a patient includes advancing a wire guide in an upstream direction through a vascular access sheath extending into an artery of the patient at a percutaneous entry point in the lower leg, and guiding a treatment mechanism into a constriction in the artery via sliding a catheter coupled with the treatment mechanism over the wire guide from the percutaneous entry point. The method further includes increasing a flow of blood in a downstream direction through the artery at least in part by dilating the constriction with the treatment mechanism, and withdrawing the catheter from the patient at the percutaneous entry point via sliding the catheter in the downstream direction through the vascular access sheath.

In another aspect, a catheter for treating lower leg ischemia in a patient includes a compound catheter body having a proximal body end and a distal body end, the compound catheter body further having an outer tubular body piece defining a longitudinal axis, and a coaxial inner tubular body piece, the outer and inner tubular body pieces together defining an inflation lumen extending axially between the proximal and distal body ends. The catheter further includes a balloon coupled with the compound catheter body, the balloon having a proximal neck attached to the outer tubular body piece, a distal neck attached to the inner tubular body piece, and the balloon defining a cavity in fluid communication with the inflation lumen. The outer tubular body piece further defines an inlet port to the inflation lumen for connecting with a supply of inflation fluid, and the inner tubular body piece further defines a wire guide lumen opening at each of the proximal and distal body ends such that the catheter may be slid over a wire guide extending through the compound catheter body. The balloon is in a rest configuration and defines a first outer diameter dimension which is equal to about 0.7 mm or less, such that the catheter may be advanced into or withdrawn from the patient through a vascular access sheath extending into an artery at a percutaneous entry point in the patient's lower leg, and wherein the balloon is inflatable via the inflation fluid to an expanded configuration at which the balloon defines a second outer diameter dimension which is equal to about 1.2 mm or greater, for dilating a constriction in the artery.

In still another aspect, a method of treating lower leg ischemia via retrograde access to a lower leg artery in a patient includes sliding a vascular access sheath over a first wire guide extending into the artery at a percutaneous entry point in the patient's lower leg, the vascular access sheath having an outer diameter dimension less than about 2 mm and an inner diameter dimension greater than about 1 mm. The method further includes advancing a second wire guide through the vascular access sheath from the percutaneous entry point such that a tip of the second wire guide crosses a constriction in the artery located upstream of the vascular access sheath. The method further includes guiding a catheter into a constriction in the artery via sliding the catheter over the second wire guide from the percutaneous entry point, the catheter having an outer diameter dimension less than about 0.7 mm, and increasing a flow of blood in the downstream direction through the artery at least in part by dilating the constriction with a treatment mechanism of the catheter. The method further includes withdrawing the catheter from the patient at the percutaneous entry point, including sliding the catheter through the vascular access sheath such that the artery is protected from irritation.

DETAILED DESCRIPTION

Figure 1:
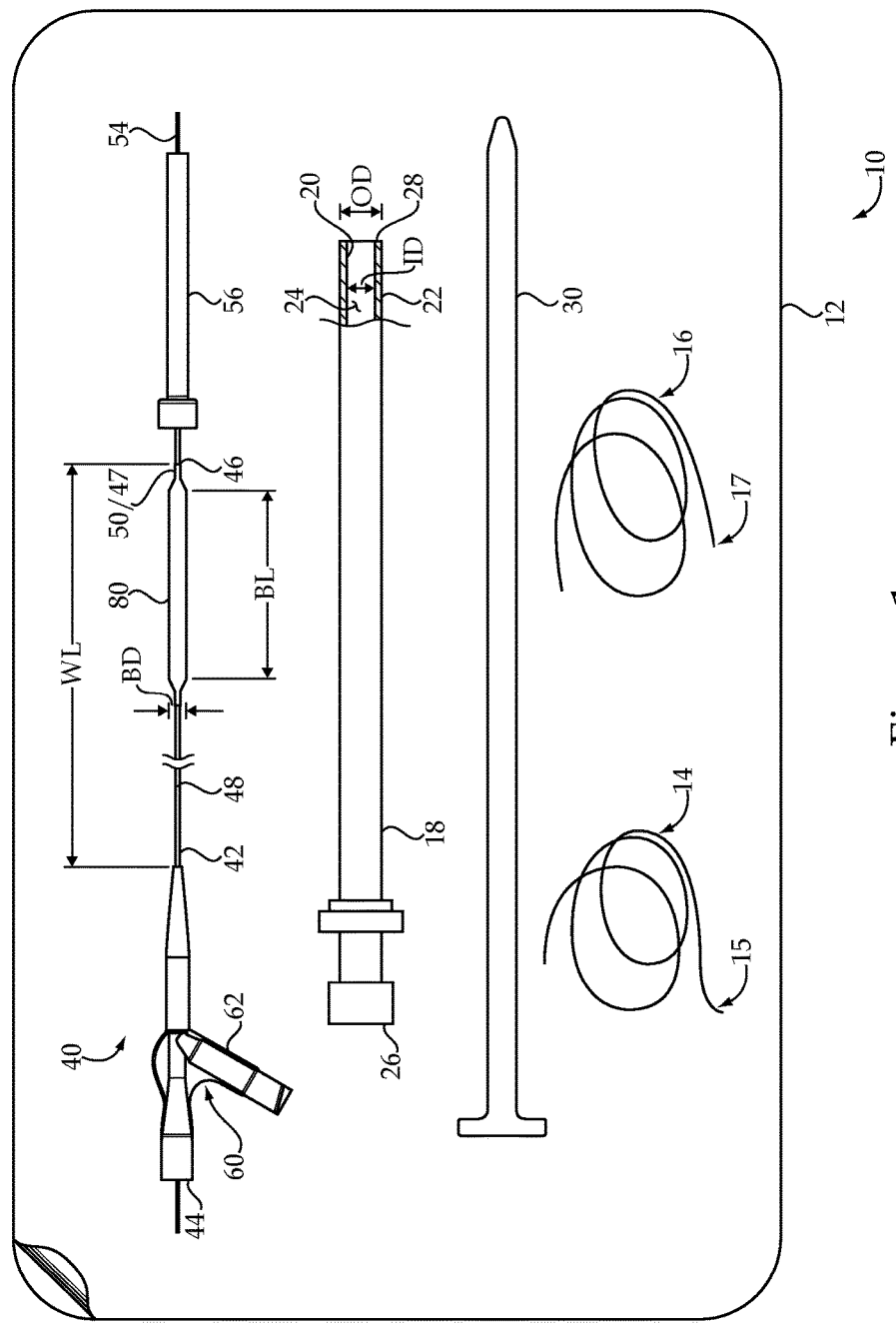
FIG. 1 is a diagrammatic view of a system for treating lower leg ischemia, according to one embodiment.

Referring to FIG. 1, there is shown a treatment system 10 according to one embodiment. Treatment system 10 includes a number of components which may be provided as a packaged set within a sterile, peel-open package 12. In performing a treatment procedure on a patient, some or all of the components of treatment system 10 may be used, depending upon the specifics of the procedure to be performed. The components shown in FIG. 1 might of course be separately packaged, and treatment system 10 might also include components in addition to those shown, provided as part of a packaged system or routinely available in clinical practice. As will be further apparent from the following description, treatment system 10 may be uniquely configured for treating conditions such as lower leg ischemia in a patient, particularly by way of enabling the dilation of a constriction within an artery in a patient's lower leg from a retrograde access point with reduced risk of irritation and spasm of the artery. As used herein, the terms "constriction," "occlusion," and "lesion" are to be given their art-recognized meanings, and are used generally interchangeably. The terms "retrograde" and "upstream" mean against the flow of blood, or where no flow of blood exists, toward the heart, whereas "anterograde" and "downstream" mean with the flow of blood or away from the heart.

System 10 may include a first wire guide 14 which is adapted for accessing a vessel such as an artery in a patient in a conventional manner. Wire guide 14 may include a floppy distal tip 15, and may be relatively thin and flexible such that it may be readily passed through a piercing needle at a percutaneous entry point to the patient's vasculature, and advanced into the vessel to provide an initial guide for subsequent placement of treatment devices. System 10 may also include a second wire guide 16 which is a relatively more rigid crossing wire, having a less floppy distal tip 17, and being adapted for pushing through occlusive material within a vessel, as further described herein. System 10 may further include a vascular access sheath 18 having an outer surface 22, and an inner surface 20 defining a lumen 24 extending longitudinally between a first sheath end 26 and a second sheath end 28. System 10 may still further include a stiffening dilator 30 which is configured for positioning within vascular access sheath 18 when placing sheath 18 within a vessel in the patient. As further described herein, an assembly of vascular access sheath 18 and stiffening dilator 30 may be slid over wire guide 14 to position sheath 18 as desired, after which dilator 30 may be withdrawn. Sheath 18 may be used as a conduit for passing treatment devices and the like, or liquid treatment agents such as a vasodilator, into or out of the patient. Vascular access sheath 18 may be sized to enable accessing, and passing of treatment mechanisms into and out of, relatively small vessels in the human anatomy such as those having an internal vessel diameter of about 2 mm or less.

In one embodiment, vascular access sheath 18 may be used to access arteries in a patient's lower leg, i.e. below the knee, such as the pedis dorsalis or "pedal" artery, or the anterior or posterior tibial arteries, although the present disclosure is not thereby limited. To this end, vascular access sheath 18 may define an outer diameter dimension OD which is equal to about 2 mm or less, and which may be equal to about 1.88 mm or less. The small size of vascular access sheath 18 enables it to be readily passed through a patient's skin directly into a small artery such as the pedal artery via an entry point in the patient's foot or ankle. An inner diameter dimension ID of sheath 18 may be equal to about 1 mm or greater, up to about 1.6 mm in certain embodiments. Dimension ID may be equal to between about 0.8 mm and about 1.2 mm, and in certain embodiments equal to between about 0.91 mm and about 1.12 mm. As used herein, the term "about" should be understood in the context of a number of significant digits. Accordingly, about 2 mm means between 1.5 mm and 2.4 mm, about 1.88 mm means between 1.875 mm and 1.884 mm. As further discussed herein, treatment mechanisms passed through sheath 18 may be sized very small compared to conventional mechanisms of comparable function, facilitating heretofore impossible or impracticable treatment techniques using retrograde access to vessels in a patient's lower leg.

System 10 may further include a catheter 40 configured for treating lower leg ischemia in a patient, such as by passing catheter 40 through sheath 18 via a percutaneous entry point in the patient's lower leg. Catheter 40 may include a compound catheter body 42 having a proximal body end 44 and a distal body end 46. Compound catheter body 42 may further include an outer tubular body piece 48 and an inner tubular body piece 50 arranged coaxially with outer tubular body piece 48. Outer tubular body piece 48 may define a longitudinal axis, illustrated in drawings further described and discussed below.

Catheter 40 may further include a manifold 60 coupled with or part of catheter body 42. Manifold 60 may include a housing 61 having a sidearm 62, the purposes of which are further discussed below. Catheter 40 further includes a treatment mechanism 80 which may comprise a balloon configured for performing angioplasty on a vessel in a patient as further described herein. Balloon 80 may include a proximal neck 82 attached to outer tubular body piece 48, and a distal neck 84 attached to inner tubular body piece 50. In the illustration of FIG. 1, only a small part of inner tubular body piece 50 is visible, at distal body end 46, as most of body piece 50 is obscured by body piece 48, manifold 60, and balloon 80. A tip piece 47 may be coupled with outer tubular body piece 50 and includes the terminal tip of distal end 46. In FIG. 1, catheter 40 is shown as it might appear prepared for shipping. A shipping stylet 54 extends all the way through catheter body 42 for conventional purposes. A balloon protector 56 is also provided, and may be slid over balloon 80 to protect it from stress or damage during shipping and storage.

As mentioned above, treatment mechanisms passed through vascular access sheath 18 and into a vessel in the body may be sized very small, and such that they can be passed through lumen 24 and ultimately into small vessels in a patient. To this end, balloon 80 may define a first outer diameter dimension shown as dimension BD in FIG. 1 when balloon 80 is in a rest, or uninflated state. Outer diameter dimension BD may be equal to about 0.7 mm or less, and in one practical implementation strategy may be equal to about 0.64 mm or less. Since dimension BD will typically be the widest part of catheter 40 which is to be passed into a patient, the size of dimension BD when balloon 80 is uninflated typically determines at least in part the size of occlusions and the like which can be treated via catheter 40, and also determines what size sheaths such as vascular access sheath 18 with which catheter 40 can be practicably used. As further explained herein, one application of the present disclosure relates to placing catheter 40 within an artery of a patient via a percutaneous entry point in the patient's lower leg, and taking advantage of the benefits of using sheath 18 as a protective barrier to limit irritating the artery. As such catheter 40 may be sized such that it can be readily advanced into or withdrawn from the patient through vascular access sheath 18, while maintaining sheath 18 in a fixed position. The small size of dimension BD leads to these capabilities. A suitable slip coating might be applied to balloon 80 and other parts of catheter 40 to further facilitate sliding catheter 40 through sheath 18.

When balloon 80 is inflated via an inflation fluid to an expanded configuration, balloon 80 may define a second outer diameter dimension which is equal to about 1.2 mm or greater, such as for dilating a constriction in an artery. The second outer diameter dimension may further be equal to about 1.28 mm or greater, and in a practical implementation strategy may be equal to between about 1.30 mm and about 1.70 mm. Also shown in FIG. 1 is a working length dimension WL which extends from a distal end of housing 61 to the terminal distal end of tip piece 47, and may be equal to about 70 cm plus or minus 4 cm, although the present disclosure is not thereby limited. Still another dimension which includes a balloon length BL is shown in FIG. 1, and may be equal to between about 19 mm and about 41 mm in certain embodiments. It is expected that, depending upon the length of an occluded region in an artery to be treated, balloon length BL might be significantly larger, possibly up to about 200 mm.

Figure 2:
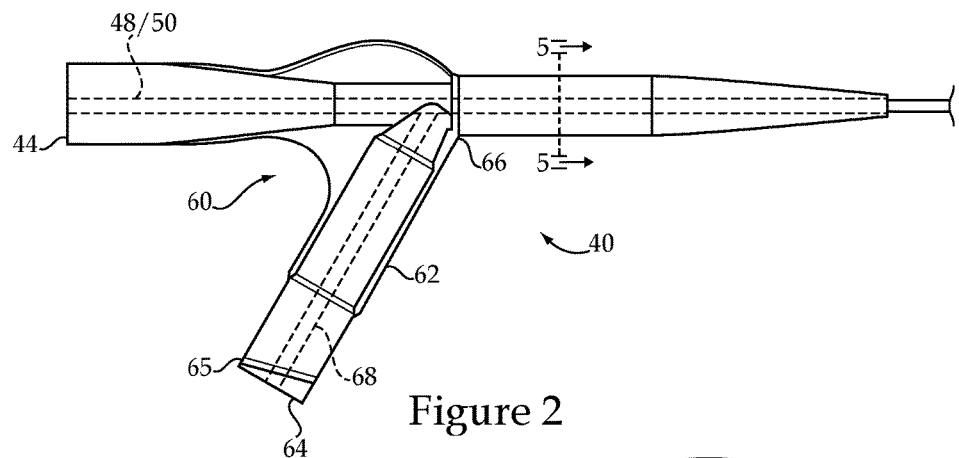
FIG. 2 is a side diagrammatic view of a portion of a catheter used in the system of FIG. 1.
Figure 3:
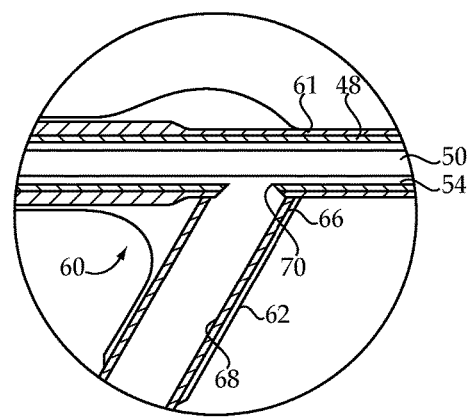
FIG. 3 is a sectioned side diagrammatic view of a portion of the catheter of FIG. 2.

Referring also now to FIG. 2, there is shown a close up view of a portion of catheter 40, and in particular illustrating manifold 60. In FIG. 2, the dashed lines indicated via reference numerals 48/50 represent both of outer tubular body piece and inner tubular body piece 50. The dashed lines indicated via reference numeral 68 identify an inflation fluid conduit extending between a first end 64 of side arm 62 having a fitting 65, and a second end 66. Referring also to FIG. 3, there is shown a partially sectioned side diagrammatic view of a portion of FIG. 2, in which an inflation lumen 54 defined by outer tubular body piece 48 and inner tubular body piece 50 is shown connecting with inflation fluid conduit 68 by way of an inlet port 70 defined by outer tubular body piece 48. This fluid connection allows inflation lumen 54 to be connected with a supply of inflation fluid coupled with fitting 65 for inflating balloon 80, as further described herein. Sidearm 62 may be attached to outer tubular body piece 48 such as by way of an adhesive or other suitable bond 69 with material of housing 61, and/or with material of outer tubular body piece 48.

Figure 4:
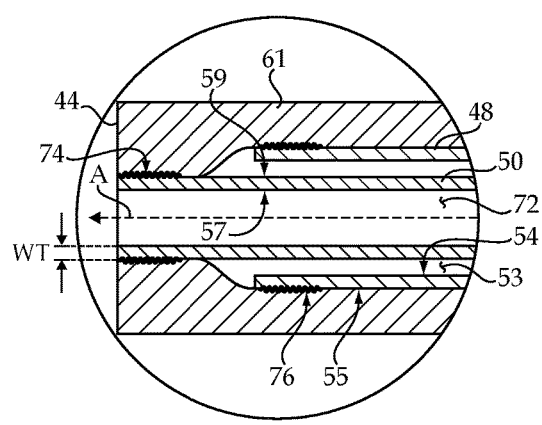
FIG. 4 is a sectioned side diagrammatic view of another portion of the catheter of FIG. 2.

Referring now to FIG. 4, there is shown a sectioned view of a portion of catheter 40 which includes proximal body end 44. As noted above, outer tubular body piece 48 and inner tubular body piece 50 are coaxially arranged about a common longitudinal axis A. In the embodiment illustrated in FIG. 4, outer tubular body piece 48 is attached to housing 61 via a bond 76 which includes a suitable adhesive such as a UV cured adhesive, or other type of bond. Inner tubular body piece 50 is also attached to housing 61 at a bond 74 of any suitable type such that inflation lumen 54 is closed at proximal body end 44. It may be noted from FIG. 4 (and FIG. 5, discussed below) that inflation lumen 54 may include a generally circular shape extending between and defined by an outer surface 59 of inner tubular body piece 50 and an inner surface 53 of outer tubular body piece 48. An outer surface 55 of outer tubular body piece 48 adjoins material of housing 61, whereas an inner surface 57 of inner tubular body piece 50 defines a longitudinally extending wire guide lumen 72 which opens at proximal body end 44, and also at distal body end 46 such that catheter 40 may be slid over a wire guide extending all the way through compound catheter body 42, as further described herein.

Consistent with principles of forming catheter 40 to be small enough yet robust enough for practicable retrograde access and treatment of vessels in a patient's lower leg, certain materials may be advantageously used in constructing certain parts of catheter body 42 such that relatively small size and modest material thicknesses may be used without unduly sacrificing strength. To this end, a dimension WT is shown in FIG. 4 and includes a wall thickness in a radial direction from outer surface 59 to inner surface 57 of inner tubular body piece 50. Outer tubular body piece 48 may include a similarly dimensioned wall thickness from outer surface 55 to inner surface 53. Wall thickness WT may be equal to between about 0.03 mm and about 0.06 mm, and in a practical implementation strategy may be equal to between about 0.046 mm and about 0.05 mm.

Figure 5:
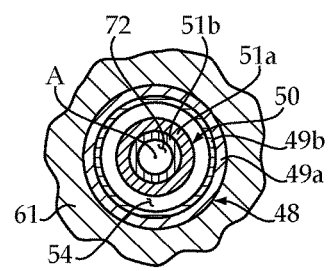
FIG. 5 is a sectioned view taken along line 5-5 of FIG. 2.

As alluded to above, the selection of certain materials for use in constructing body pieces 48 and 50 can advantageously impart desirable properties of strength, small size and thin walls, biocompatibility, and lubricity. Referring now to FIG. 5, there is shown a sectioned view along line 5-5 of FIG. 2. It should be noted that FIG. 5 illustrates each of body pieces 48 and 50 as having two layers of material, whereas FIG. 4 illustrates body pieces 48 and 50 as having only a single layer of material. In certain embodiments, body pieces 48 and 50 will indeed include two layers of material, but are illustrated alternatively to such in FIG. 4 for purposes of clarity. Moreover, the relative thicknesses shown are merely for illustrative purposes, as certain material layers may be so thin as to make illustration difficult. Outer tubular body piece 48 may include an outer layer of material 49a and an inner layer of material 49b, whereas body piece 50 may include an outer layer of material 51a and an inner layer of material 51b. In one embodiment, each of outer layers 49a and 51a may include a polyimide, thermoset nylon base material, while inner layers 49b and 51b may include a coating material such as a material containing PEEK (polyether ether ketone), and in one embodiment a PEEK and fluoropolymer composite. Inner layers 49b and 51b may be several times thinner than outer layers 49a and 51a. Layers 49a and 51a may be formed as extrusions, and then coated with layers 49b and 51b via known techniques. Other known polymeric materials, and composites, may be used as the base material or coating material.

Figure 6:
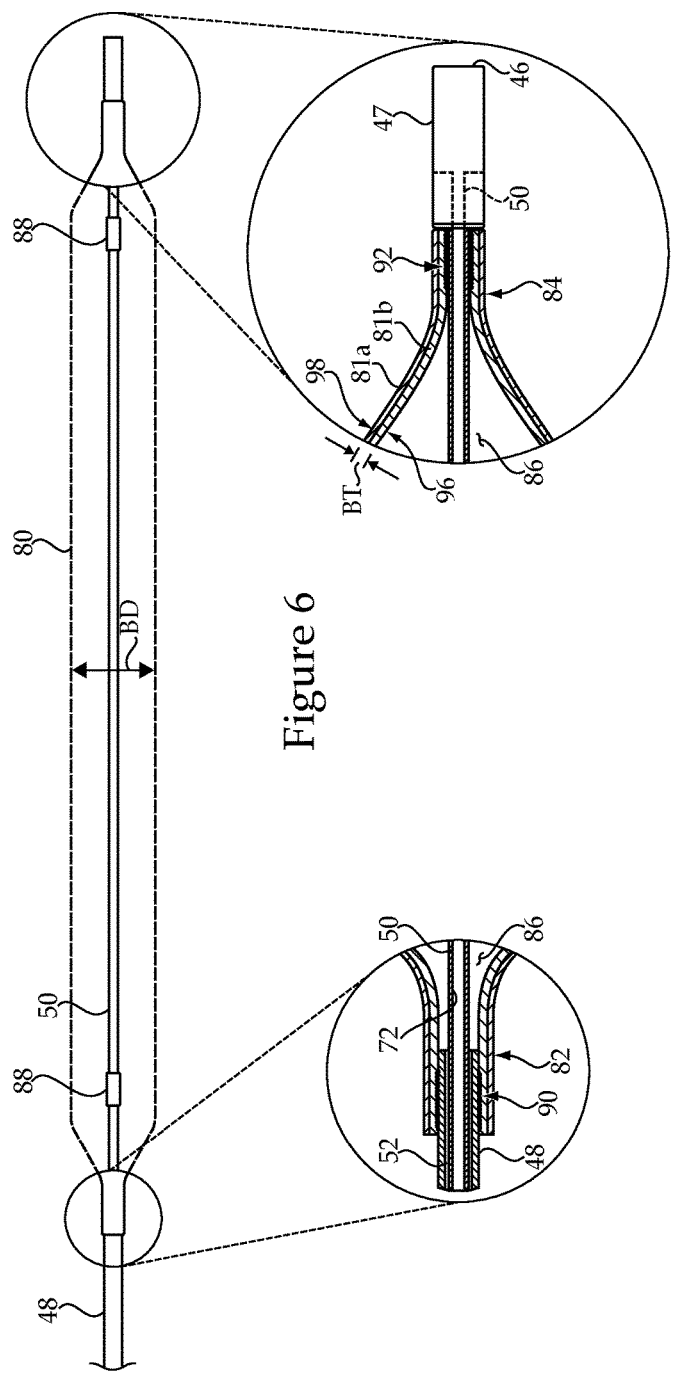
FIG. 6 is a side diagrammatic view of a treatment mechanism suitable for use with the catheter of FIG. 2, including detailed enlargements.

Referring now to FIG. 6, there is shown a view of balloon 80 in phantom such that inner tubular body piece 50 is shown extending therethrough. It may be noted that a first and second radiopaque marker band 88 are located at proximal and distal locations upon body piece 50, and within balloon 80. FIG. 6 also includes a first detailed enlargement which includes proximal neck 82 of balloon 80, and illustrates a bond 90 such as an adhesive bond between proximal neck 82 and outer body piece 48. A second detailed enlargement shows distal balloon neck 84, and illustrates a similar bond 92 between distal balloon neck 84 and inner body piece 50. It may also be noted that inner body piece 50 extends distally of balloon 80 such that it is positioned partially within tip piece 47. Each of the detailed enlargements in FIG. 6 shows a portion of a cavity 86 defined by balloon 80 and in fluid communication with inflation lumen 52.

Figure 7:
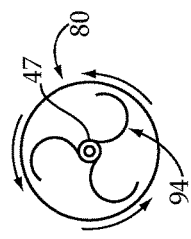
FIG. 7 is an end view of the treatment mechanism of FIG. 6.

In one embodiment, balloon 80 may include a double wall balloon having an outer material layer 81a which includes an outer surface 98, and an inner material layer 81b which includes an inner surface 96. Each of layers 81a and 81b may be formed of nylon, for instance, although the present disclosure is not thereby limited. Balloon 80 may further include a wall thickness BT from inner surface 96 to outer surface 98 which is between about 0.02 mm and about 0.03 mm, and such that balloon 80 defines a burst pressure greater than about 25 atmospheres. Referring also to FIG. 7 there is shown an end view of balloon 80. Balloon 80 may include a plurality of longitudinal folds, and in one embodiment may include a total of three longitudinal folds 94. The arrows in FIG. 7 indicate an approximate direction of folding of the material of balloon 80. Upon inflation, balloon 80 will unfold to assume its expanded configuration.

INDUSTRIAL APPLICABILITY

Figure 8:
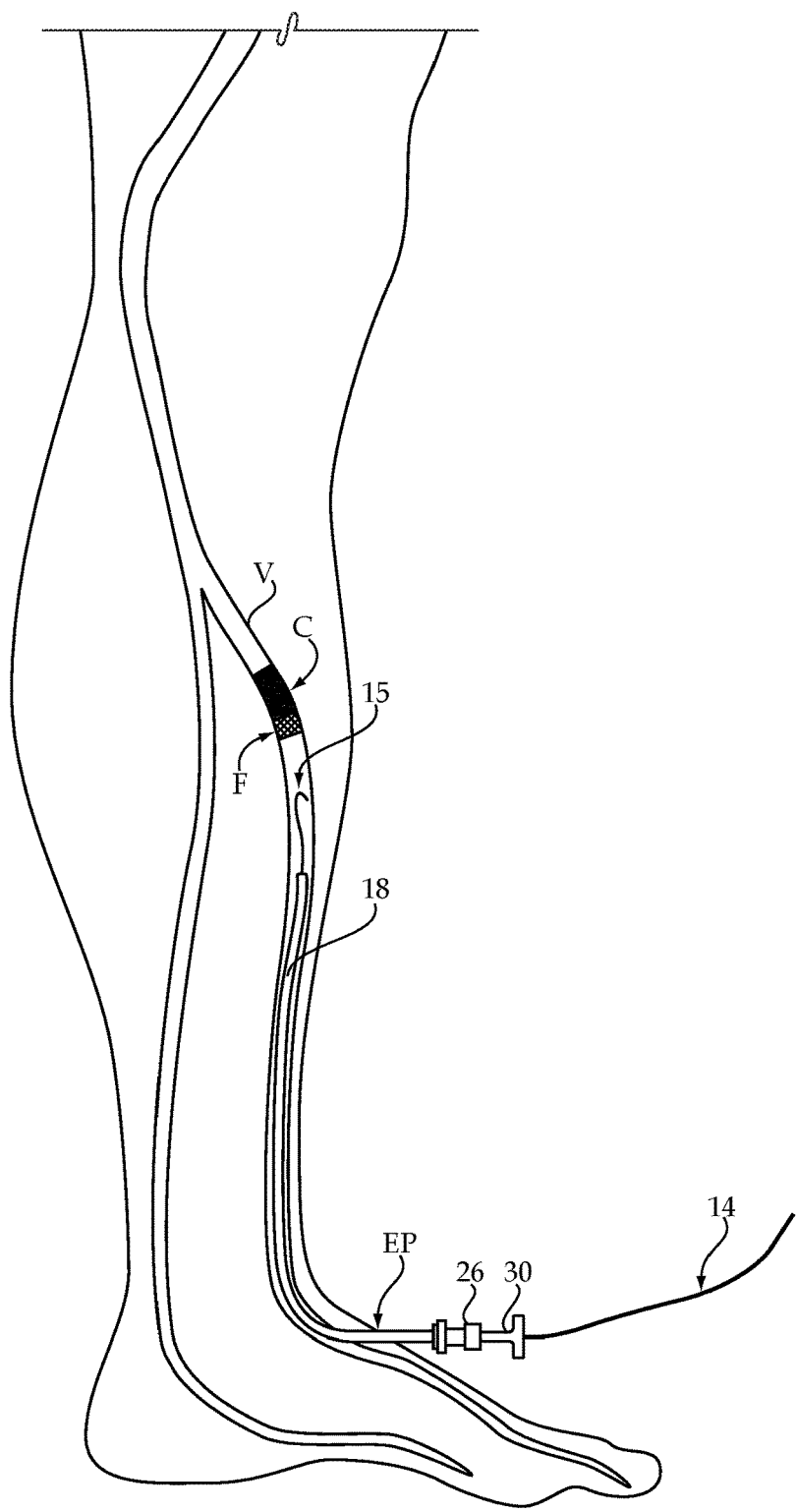
FIG. 8 is a side diagrammatic view at one stage of a treatment procedure, according to the present disclosure.

A treatment procedure for lower leg ischemia according to the present disclosure may commence by passing a suitable piercing needle or the like through a patient's skin and into the lumen of an artery of the patient. A suitable wire guide may then be passed through the piercing needle into the artery, and the piercing needle withdrawn while leaving the wire guide in place. For establishing initial access into the vasculature, a relatively soft or floppy wire guide may be used. Referring now to FIG. 8, there is shown wire guide 14 having been passed into an artery V of a patient at an entry point EP in the patient's foot or ankle. Vascular access sheath 18 with stiffening dilator 30 positioned therein has been advanced as an assembly into artery V in an upstream direction toward a constriction C. With vascular access sheath 18 positioned as shown, it may serve as a conduit for passing various devices into artery V, and also for withdrawing such devices, typically once dilator 30 has been removed.

Figure 9:
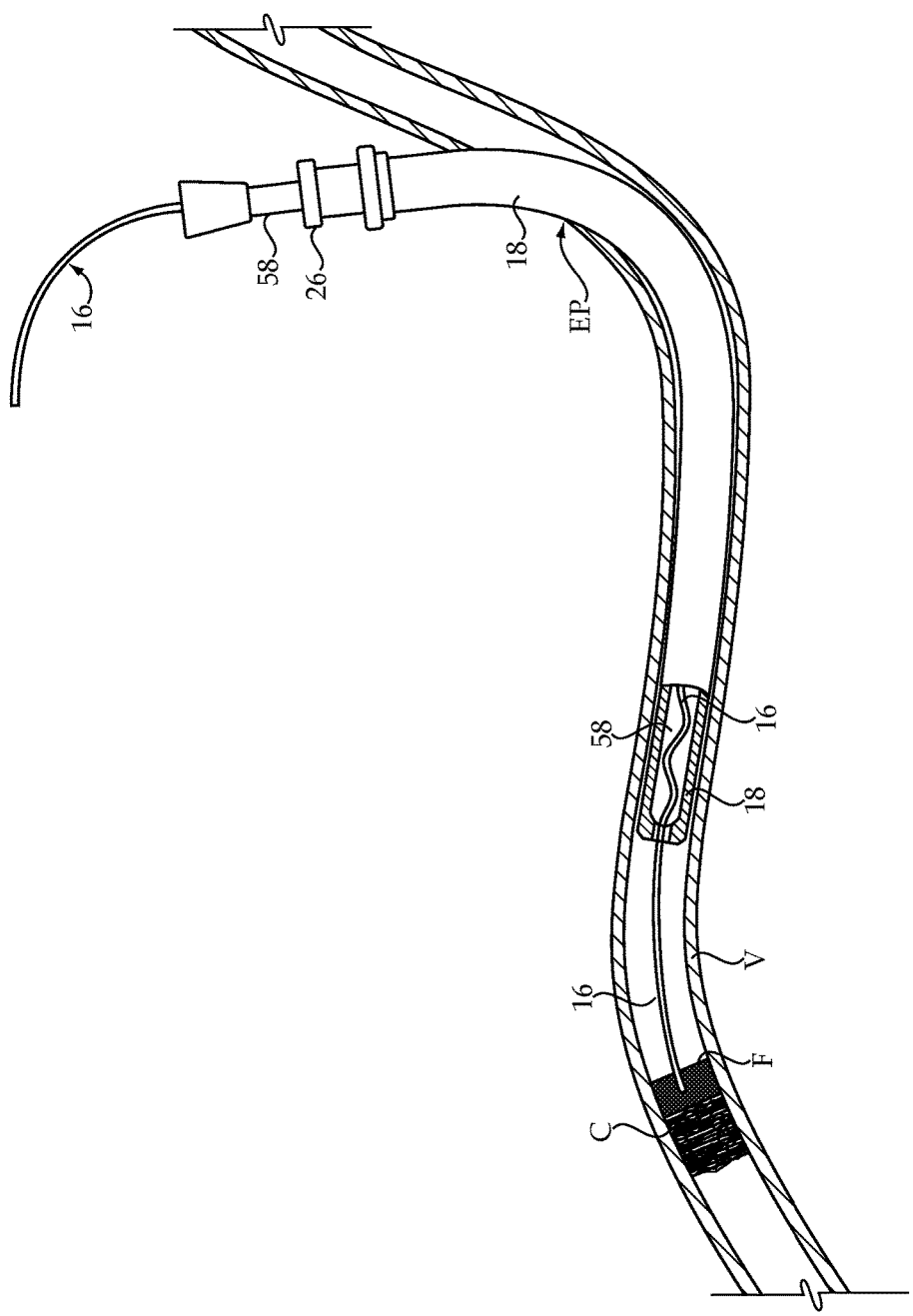
FIG. 9 is a side diagrammatic view of another stage of the treatment procedure.

Referring also to FIG. 9, there is shown vascular access sheath positioned similarly as in FIG. 8. Second wire guide 16 has been swapped for wire guide 14, and has been advanced in an upstream direction through sheath 18. At the state depicted in FIG. 9, wire guide 16 has been pushed upstream such that tip 17 has begun to cross constriction C, and is being urged through material occluding artery V. In particular, wire guide 16 is being used to cross constriction C via puncturing a fibrous cap of material F located at a downstream end of constriction C. From the state depicted in FIG. 9, wire guide 16 may be further advanced in an upstream direction to cross all the way through constriction C. Tip 17 may be maintained within the true lumen of artery V during crossing constriction C, in contrast to other techniques where a crossing wire is taken subintimally.

Also shown in FIG. 9 is a microcatheter 58 which extends at least part way through sheath 18, and may be used to limit buckling of wire guide 16 in response to a resistance of fibrous cap F during crossing constriction C. Sheath 18 may be relatively flexible, whereas microcatheter 58 may be relatively less flexible and thus capable of resisting the tendency for wire guide 16 to bend sideways as it is pushed against and through the material occluding the artery. Placing microcatheter 58 within sheath 18 may not only support wire guide 16 to enhanceability to cross constriction C, but may also reduce a tendency for sliding movement and buckling of wire guide 16 to irritate the artery.

Figure 10:
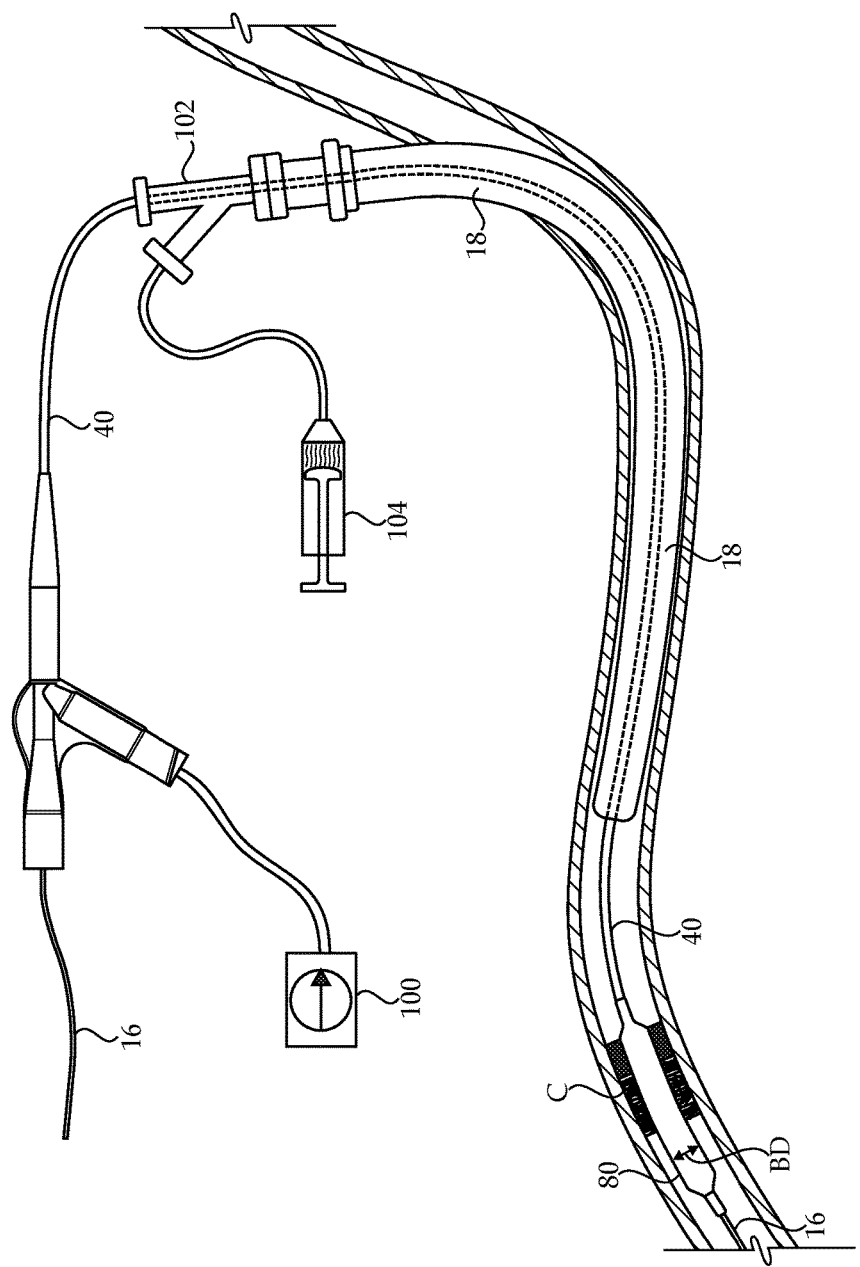
FIG. 10 is a side diagrammatic view of yet another stage of the treatment procedure.

Referring now to FIG. 10, after crossing the constriction with wire guide 16, a treatment mechanism such as balloon 80 of catheter 40 may be guided into the constriction via sliding catheter 40 over wire guide 16 from the percutaneous entry point. In FIG. 10, balloon 80 is shown having been inflated via supplying a pressurized inflation fluid to catheter 40 from a pump 100 or other suitable source of pressurized inflation fluid. An inflation pressure may be up to about 25 atmospheres. Inflating balloon 80 may dilate the constriction such that a flow of blood in a downstream direction through the artery is increased from a pre-dilation state once balloon 80 is removed. Subsequent to dilating the constriction, balloon 80 may be deflated and withdrawn from the patient by withdrawing catheter 40 at the percutaneous entry point, in particular sliding catheter 40 in the downstream direction through sheath 18 while sheath 18 is maintained stationary. Also shown in FIG. 10 is a Y-fitting 102 coupled with sheath 18, and having a syringe 104 connected therewith. Syringe 104 may contain a fluid such as a vasodilator which is injected into the artery through sheath 18. Injecting the vasodilator may commence subsequent to withdrawing catheter 40 from the patient, but prior to withdrawing sheath 18 and wire guide 16. In certain instances, vasodilator may be injected through sheath 18 and around catheter 40 while catheter 40 remains resident within sheath 18, or even prior to placing catheter 40 within the patient.

Physicians have attempted a wide variety of techniques for improving or restoring blood flow to the lower extremities where insufficient or zero blood flow is taking place. In the case of certain conditions, such as chronic total occlusions in arteries of the lower leg, known techniques are generally some form of the three different approaches discussed above. In some instances, a physician may attempt to reach a treatment area from an upstream access point such as the femoral artery in the same leg to be treated, or from the femoral artery in the opposite leg, in the latter case moving treatment devices in an upstream direction through the opposite femoral artery and then downstream toward the treatment site. In other instances, physicians may work from two entry points, one downstream a lesion to accommodate a wire guide for crossing the lesion in a retrograde direction and one upstream for introducing a treatment mechanism such as a balloon catheter in an anterograde direction. In this second class of techniques, in connection with which the term "arterial flossing" is commonly used, a wire guide may extend into the patient at one of the access points, through the vasculature, and out of the patient at the other access point. Yet a third general approach attempts to treat an occlusion by "bare backing" a catheter through a downstream entry point in the foot or ankle. Each of these approaches has its own risks and disadvantages.

As noted above, patient anatomy can be inconsistent with establishing an upstream access point. Moreover, difficulty in crossing the lesion from an upstream access point is also common. In the case of arterial flossing, it can be quite challenging for a physician to snare a wire guide passed upstream through a lesion in the lower leg such that the wire guide can be advanced to the upstream entry point and out of the patient and, moreover, post-procedure treatment requires dealing with multiple entry wounds. In the case of bare backing, it is common for a patient's arteries to spasm due to the friction and irritation associated with pushing a catheter through a small artery close in size to the catheter itself. In view of the teachings of the present disclosure these concerns are reduced or eliminated altogether.

Since catheter 40 and other catheters contemplated herein may be quite small, in particular having very small diameter, low profile balloons, it is possible for sheath 18 to provide a protective barrier between the vessel and catheter 40 as well as wire guide 14. Rubbing and friction associated with earlier techniques is much reduced, and thus the risk of spasming of the artery is ameliorated. As compared with upstream access, as well as arterial flossing, the presently disclosed procedures are substantially simpler and less dependent upon consistency with a patient's anatomy. Finally, post-procedure homeostasis can easily be achieved by the simple application of pressure at the single entry point, such as with one finger, thus reducing post-procedure observation time.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A method of treating lower leg ischemia in a patient comprising the steps of:
    advancing a wire guide in an upstream direction through a vascular access sheath extending into a lower leg artery of the patient at a percutaneous entry point in a lower leg;
    guiding a treatment mechanism in the upstream direction into a constriction in the artery via sliding a catheter coupled with the treatment mechanism over the wire guide from the percutaneous entry point;
    increasing a flow of blood in a downstream direction through the artery at least in part by dilating the constriction with the treatment mechanism; and
    withdrawing the catheter from the patient at the percutaneous entry point via sliding the catheter in the downstream direction through the vascular access sheath.

2. The method of claim 1 further comprising a step of crossing the constriction at least in part by pushing a tip of the wire guide through material occluding the artery at a location upstream of the vascular access sheath.

3. The method of claim 2 wherein the step of crossing further includes puncturing a fibrous cap of material located at a downstream end of the constriction while maintaining the tip of the wire guide within a true lumen of the artery.

4. The method of claim 3 further comprising a step of limiting buckling of the wire guide in response to a resistance of the fibrous cap of material during the step of crossing at least in part via a microcatheter positioned to provide a barrier between the wire guide and the vascular access sheath.

5. The method of claim 2 wherein the treatment mechanism includes a balloon, and the step of increasing a flow of blood includes dilating the constriction by inflating the balloon.

6. The method of claim 1 further comprising a step of injecting a vasodilator into the artery through the vascular access sheath.

7. The method of claim 6 wherein the step of injecting occurs subsequent to the step of withdrawing.

8. The method of claim 1 further comprising a step of establishing the percutaneous entry point in a foot or an ankle of the patient.

9. The method of claim 8 wherein the step of establishing includes establishing the percutaneous entry point into a pedal artery.

10. A method of treating lower leg ischemia via retrograde access through a lower leg artery in a patient comprising the steps of:
    sliding a vascular access sheath over a first wire guide extending into the artery at a percutaneous entry point in a lower leg of the patient, the vascular access sheath having an outer diameter dimension less than about 2 mm and an inner diameter dimension greater than about 1 mm;

advancing a second wire guide through the vascular access sheath from the percutaneous entry point in an upstream direction such that a tip of the second wire guide crosses a constriction in the artery located upstream of the vascular access sheath;

guiding a catheter into the constriction in the artery in the upstream direction via sliding the catheter over the second wire guide from the percutaneous entry point, the catheter having an outer diameter dimension less than about 0.7 mm;

increasing a flow of blood in a downstream direction through the artery at least in part by dilating the constriction with a treatment mechanism of the catheter; and withdrawing the catheter from the patient at the percutaneous entry point, including sliding the catheter through the vascular access sheath such that the artery is protected from irritation.

11. The method of claim 10 wherein the step of sliding the vascular access sheath further includes sliding an assembly of the vascular access sheath and a stiffening dilator over the first wire guide at the percutaneous entry point into a pedal artery.

12. The method of claim 11 wherein the step of increasing a flow of blood includes increasing the flow of blood via dilating the constriction with a balloon of the treatment mechanism.

13. A method of treating lower leg ischemia in a patient comprising the steps of:

advancing a wire guide in an upstream direction through a vascular access sheath extending into a lower leg artery of the patient at a percutaneous entry point in a lower leg;

limiting buckling of the wire guide at least in part by positioning a microcatheter to provide a barrier between the wire guide and the vascular access sheath;

guiding a treatment mechanism into a constriction in the artery in the upstream direction via sliding a catheter coupled with the treatment mechanism over the wire guide from the percutaneous entry point in the upstream direction;

increasing a flow of blood in a downstream direction through the artery at least in part by dilating the constriction with the treatment mechanism; and withdrawing the catheter from the patient at the percutaneous entry point via sliding the catheter in the downstream direction through the vascular access sheath.

14. The method of claim 13 further comprising a step of crossing the constriction at least in part by pushing a tip of the wire guide through material occluding the artery at a location upstream of the vascular access sheath.

15. The method of claim 14 wherein the step of crossing further includes puncturing a fibrous cap of material located at a downstream end of the constriction while maintaining the tip of the wire guide within a true lumen of the artery.

16. The method of claim 15 wherein the step of limiting buckling of the wire guide is performed during the step of crossing responsive to a resistance of the fibrous cap of material.

17. The method of claim 14 wherein the treatment mechanism includes a balloon, and the step of increasing a flow of blood includes dilating the constriction by inflating the balloon.

18. The method of claim 13 further comprising a step of injecting a vasodilator into the artery through the vascular access sheath.

19. The method of claim 13 further comprising a step of establishing the percutaneous entry point into a pedal artery in a foot or an ankle of the patient.

* * * * *